US009677995B2

(12) United States Patent
Spanier et al.

(10) Patent No.: US 9,677,995 B2
(45) Date of Patent: Jun. 13, 2017

(54) SAMPLE CELL FILLING DEVICE FOR USE REMOTELY FROM A POLARIMETER AND METHOD OF USING THE SAME

(71) Applicant: Rudolph Research Analytical Corporation, Hackettstown, NJ (US)

(72) Inventors: Richard C. Spanier, Chester, NJ (US); Jeff Wagner, Long Valley, NJ (US)

(73) Assignee: RUDOLPH RESEARCH ANALYTICAL CORPORATION, Hackettstown, NJ (US)

( * ) Notice: Subject to any disclaimer, the term of this patent is extended or adjusted under 35 U.S.C. 154(b) by 201 days.

(21) Appl. No.: 14/595,266

(22) Filed: Jan. 13, 2015

(65) Prior Publication Data

US 2016/0202176 A1    Jul. 14, 2016

(51) Int. Cl.
  *G01N 21/00*  (2006.01)
  *G01N 21/11*  (2006.01)
  *G01J 4/00*   (2006.01)
  *G01N 21/21*  (2006.01)

(52) U.S. Cl.
  CPC .............. *G01N 21/11* (2013.01); *G01J 4/00* (2013.01); *G01N 21/21* (2013.01)

(58) Field of Classification Search
  CPC  G01F 11/284; G01N 21/0303; G01N 21/553; G01N 21/896; G03B 13/24
  USPC .................... 356/440, 364, 436, 336
  See application file for complete search history.

(56) References Cited

U.S. PATENT DOCUMENTS

| | | | | |
|---|---|---|---|---|
| 1,939,088 A * | 12/1933 | Styer | .................. | G01N 21/0303 356/436 |
| 3,951,552 A * | 4/1976 | McCord | .................. | G01J 1/46 356/215 |
| 5,463,228 A * | 10/1995 | Krause | .................. | G01F 11/284 250/577 |
| 5,760,900 A * | 6/1998 | Ito | ...................... | G01N 15/1434 250/461.2 |
| 5,820,265 A * | 10/1998 | Kleinerman | ....... | G01D 5/35377 250/227.14 |
| 6,437,357 B1 * | 8/2002 | Weiss | .................. | G01N 21/896 250/223 R |
| 6,791,689 B1 * | 9/2004 | Weckstrom | ............... | G01J 3/10 356/437 |
| 7,535,571 B2 * | 5/2009 | Dietz | .................. | G01F 23/2927 356/445 |
| 8,330,959 B2 * | 12/2012 | Claypool | ............. | G01N 21/553 356/445 |
| 2010/0007783 A1 * | 1/2010 | Sato | ...................... | G03B 13/24 348/340 |

(Continued)

*Primary Examiner* — Tarifur Chowdhury
*Assistant Examiner* — Isiaka Akanbi
(74) *Attorney, Agent, or Firm* — Kaplan Breyer Schwarz, LLP

(57) ABSTRACT

A sample cell filling device for filling a sample cell to be used remotely from a polarimeter is provided. The filling device includes a liquid-sealed housing, light source and a diffuser viewing screen. The housing has a recess for receiving the sample cell, the sample cell having first and second optical windows at the respective ends. A light source transmits light from one optical window to the other optical window. A diffuser viewing screen receives light exiting from the sample cell such that light from the viewing screen can be observed by a user to determine the quality of the sample fill.

15 Claims, 2 Drawing Sheets

(56) References Cited

U.S. PATENT DOCUMENTS

2010/0267163 A1\* 10/2010 Ran .................. G01N 21/553
436/164
2015/0276581 A1\* 10/2015 Ostermeyer ........... G01N 21/01
356/367

\* cited by examiner

SAMPLE CELL FILLING DEVICE FOR USE REMOTELY FROM A POLARIMETER AND METHOD OF USING THE SAME

TECHNICAL FIELD

The present invention relates generally to polarimeters, and more particularly, a sample cell filling device for use remotely from a polarimeter.

BACKGROUND OF THE INVENTION

Polarimeters are measurement instruments used to determine the optical rotation of liquid samples. A typical arrangement includes a first optical system to project a beam of light of known polarization state through a liquid sample. The beam exiting the sample then passes into a second optical system which detects a change in polarization state induced by the liquid sample. The means of holding the liquid sample is commonly referred to as a sample cell. Sample cells often have a cylindrical inner chamber arranged coaxially with the beam. Each end of the cylindrical chamber is closed off with a transparent window to confine the liquid sample while allowing the beam to traverse the cylindrical chamber. Filling ports are typically provided near each end of the sample cell. These ports communicate with the sample chamber and allow a liquid sample to be introduced into the cylindrical chamber from one end while air displaced by the incoming liquid sample exits through the port at the opposite end.

The property being measured, optical rotation, is proportional to the length of the beam path through the sample. A cylindrical chamber with a diameter slightly larger than the beam maximizes the length of the beam path for a given volume of liquid sample, thereby maximizing the detected signal.

A disadvantage of this arrangement is that any bubbles trapped in the sample chamber may also lie in the path of the beam of light. Bubbles may be present in the liquid sample prior to injection or may be created during injection by cavitation or a momentary loss of sealing between the filling port and the injecting device. Bubbles are a source of error in measurement of the optical rotation of liquid samples and should be detected and eliminated after filling to ensure correct results. Bubbles can be eliminated by emptying and reloading the sample cell or by pushing additional liquid sample through the sample cell.

The traditional method of checking that a sample cell has been filled without bubbles is to raise the sample cell to eye level and sight along the bore of the sample chamber through the transparent windows. A more recent development is to place an electronic camera along with suitable optics inside the polarimeter to replace the action of the eye.

Both the prior art built-in camera and traditional eye methods are incompatible in some ways with modern laboratory safety practice. Modern safety practice dictates that many materials should be handled under special conditions, for example under a fume hood. Typically a central sample preparation area is provided with suitable sinks, ventilation and other safety equipment. Sample cells are filled in the preparation area, often capped, and then delivered to the various measurement instruments.

The built-in camera method delays the detection of bubbles until the samples arrive at the instrument where conditions are not suitable for elimination of bubbles. The safety equipment is absent and any spilled materials may contaminate or damage the instrument. Sample cells must shuttle between the instrument and preparation areas until a proper fill is obtained.

The eye method can be carried out in the preparation area remote from the instrument, but the filling ports of the sample cell should be securely capped before bringing possibly hazardous materials near the face and eyes. A laboratory worker may spill the contents of an uncapped sample cell as they incline the cell toward a convenient source of light.

Therefore, it would be desirable to provide a way to safely verify that sample cells are properly filled in the preparation area away from a polarimeter, preferably at work bench height or while reaching into a fume hood.

SUMMARY OF THE DISCLOSURE

According to one aspect of the present invention, a sample cell filling device for filling a sample cell to be used remotely from a polarimeter is provided. The filling device includes a liquid-sealed housing, a light source and a diffuser viewing screen. The housing has a recess for receiving the sample cell with the sample cell having a first optical window at a first end and a second optical window at a second end. A light source transmits light from the first optical window to the second optical window. A diffuser viewing screen receives light exiting from the second optical window such that light from the viewing screen can be observed by a user to determine the quality of the sample fill.

According another aspect of the present invention, a method of checking the quality of a fill in a sample cell using a sample cell filling device away from a polarimeter is provided. The method involves placing an empty sample cell in a recess of a sample cell filling device, filling the sample cell with a sample and observing the quality of the sample fill through the viewing screen. The method further includes removing the filled sample cell from the filling device when change in light, such as a non-uniform light, from the viewing screen is observed.

Advantageously, the present invention provides a device and method for filling a sample cell away from a polarimeter in a manner that is safe and convenient, and that promotes proper filling technique, easily detects bubbles, reduces spillage, and that in the event of spills is easily decontaminated.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILED DESCRIPTION OF THE INVENTION

Figure 1:
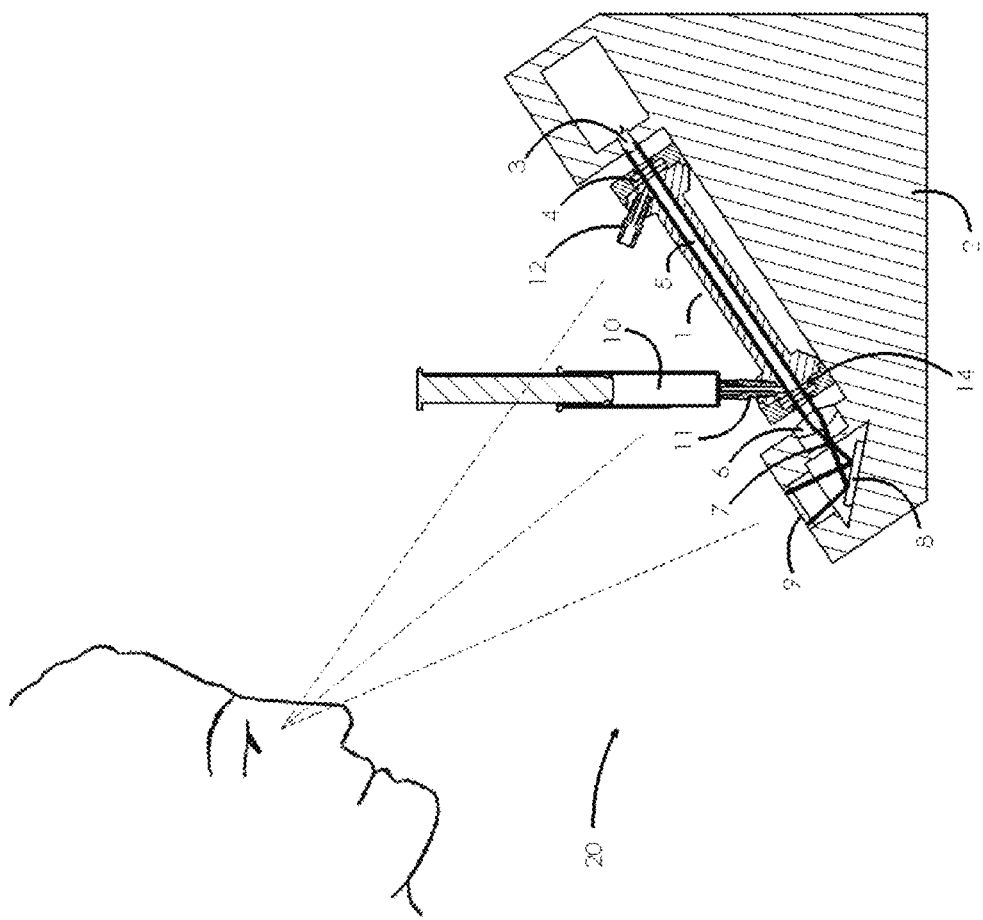
FIG. 1 illustrates a sample cell filling device according one aspect of the present invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" or "in an embodiment" in various places in the specification do not necessarily all refer to the same embodiment.

A sample cell filling device 20 according to one embodiment of the present invention is described as follows with reference to FIG. 1. The filling device 20 is designed to be used remotely from a polarimeter. A sample cell 1 removably rests on and is supported by a recess of a liquid-sealed support body/housing 2. An optical beam from light source 3 passes through transparent windows 4, 14 and sample chamber 5 of sample cell 1. After exiting sample cell 1, the optical beam is focused by focusing lens 6 through aperture 7 and onto the surface of mirror 8. The aperture 7 is positioned at a focal point of the focusing lens 6. The focusing lens provides a magnified view of the light to the viewing screen. However, any light magnifier can be used to magnify the light such as a parabolic mirror.

Mirror 8 redirects the optical beam onto the surface of a diffuser viewing screen such as a ground or frosted glass viewing screen 9 providing a magnified view to the eye of an operator. While the viewing screen in the embodiment is a ground glass, any type of a translucent material that can diffuse light can be used such as any plastic with a matt finish or even a piece of paper. In the embodiment shown, the light source 3 is an LED light. Although the light beam is preferably a collimated beam, any light source such as the LED can be used. This is because the sample in the sample cell 1 itself tends to substantially collimate the light beam.

Not shown in FIG. 1, but understood by those of ordinary skill in the art, are a sealed switch and battery connected to light source 3. A sample transferring device such as syringe 10 is engaged in a second filling port 11 forming a temporary liquid-tight seal. The second filling port 11 communicates with sample chamber 5 which in turn communicates with a first filling port 12. The optical beam from the light source 3 has an optical axis which is aligned with an optical axis of the lens 6 and aperture 7.

The recess of the filling device 20 is inclined such that when the sample cell 1 is in position and supported by the recess, the first window 4 is at a higher position than the second window 14. This is to allow air and bubbles to buoyantly migrate upward though the sample chamber and exit at the first filling port 12. Preferably, the recess of the filling device 20 positions the sample cell 1 at 10 to 50 degrees relative to a horizontal plane (e.g., base of the filling device).

In the embodiment shown, the longitudinal axis of the filling ports 11,12 of the sample cell are inclined to the longitudinal axis of the sample chamber 5 to allow a single change in the direction of the flow of the liquid sample at the transparent window. Reducing direction changes to a single bend at each window minimizes turbulence and cavitation while allowing the full volume of the sample chamber to be washed by the liquid sample with minimal dead volume. Preferably, the longitudinal axis of the filling ports 11,12 of the sample cell relative to that of the sample cell 1 is at 90-x degrees in which x is equal to the angle between the sample cell and the horizontal plane. Thus, for example, if the sample cell is supported by the filling device 20 at 30 degrees (longitudinal axis of the cell), the filling ports 11,12 are at 60 degrees relative to the longitudinal axis of the sample cell.

Figure 2B:
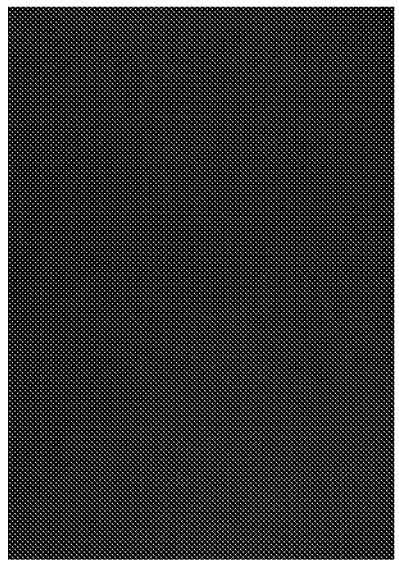
FIG. 2B illustrates a viewing screen view when the sample chamber is partially filled.
Figure 2A:
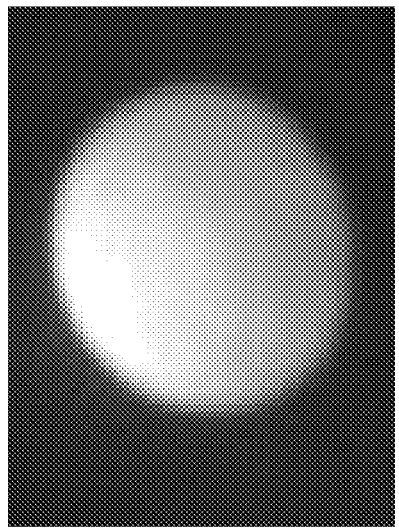
FIG. 2A illustrates a viewing screen view when the sample chamber is either empty or full.

Prior to filling the sample chamber 5, an empty sample cell will generate a uniform and bright viewing screen view as shown in FIG. 2A.

The operator, using a suitable sample transferring device such as a syringe or pipette, injects liquid sample through the second filling port 11 into the sample chamber 5. In one embodiment, the pipette or syringe is calibrated to deliver a volume sufficient to fill the sample cell without overflow. If the sample chamber 5 is partially filled with liquid sample, the free surfaces of the liquid sample will be drawn into meniscus shapes by surface tension. These surfaces will refract and reflect rays from the optical beam such that very little light arrives at the lens 6 or if it does pass through the lens 6 it will not be focused though the aperture 7. This results in a dark viewing screen 9 as shown in FIG. 2B.

When the sample chamber 5 is completely filled with the liquid sample, substantially all of the nearly collimated rays of the optical beam will arrive at the ground glass screen 9 forming a round uniform illuminated disc as shown in FIG. 2A. Based on the round uniform light at the ground glass screen 9, an operator can infer or determine a good fill in which case the filling ports 11,12 are capped and then the filled sample cell is removed from the filling device 20 to be placed in the polarimeter.

Figure 2C:
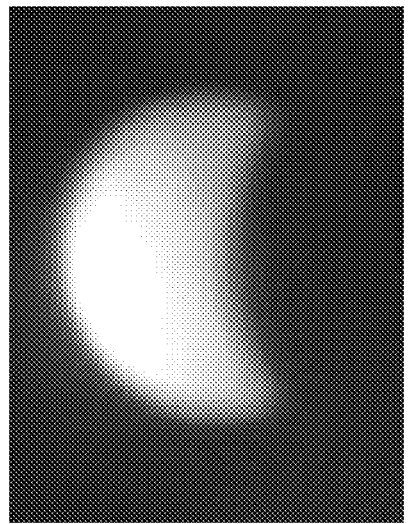
FIG. 2C illustrates a viewing screen view when the sample chamber contains an air bubble.

An operator can also infer or determine that a lack of uniformity in the illuminated disc implies that one or more bubbles are present or the sample chamber 5 is partially filled as shown in FIG. 2C. The dark spot at the lower edge of the viewing screen as shown in FIG. 2C means that a bubble is present in the sample.

Accordingly, the arrangement of the apparatus allows the operator clear sight lines to simultaneously observe the ground glass screen 9, the progress of the fill and any potential overflow at the first filling port 12, all while working at bench height or under a fume hood. The arrangement of the apparatus also facilitates a sealed construction enabling the user to wash away any spillage with water in a sink, for example, without compromising the internal components.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A sample cell filling device for filling a sample cell to be used remotely from a polarimeter comprising:
 a liquid-sealed housing having a recess for receiving and supporting the sample cell at an inclined angle, the sample cell having:
  a first optical window at a first end and a second optical window at a second end along a longitudinal axis of the sample cell; and
  a first filling port located near the first end and a second filling port located near the second end, at least one of the first and second filling ports adapted to form a temporary liquid tight seal when a sample injecting device is received therein;

a light source that transmits light from the first optical window to the second optical window; and a viewing screen, wherein light exiting the second optical window is directed to the viewing screen.

2. The sample cell filling device of claim 1, wherein the viewing screen is physically adapted to diffuse light.

3. The sample cell filling device of claim 2, wherein the viewing screen comprises ground glass.

4. The sample cell filling device of claim 1, further comprising:

a focusing lens disposed in an optical path between the second optical window and the viewing screen.

5. The sample cell filling device of claim 4, further comprising an aperture through which the light from the focusing lens passes.

6. The sample cell filling device of claim 5, further comprising a mirror disposed in an optical path between the aperture and the viewing screen to reflect the light from the aperture to the viewing screen.

7. The sample cell filling device of claim 1, further comprising a magnifier to provide a magnified view of the light.

8. The sample cell filling device of claim 1, wherein at least one of the first and second filling ports is positioned at an angle relative to the longitudinal axis of the sample cell such that the sample makes only a single change of direction when the sample is being filled in the sample cell.

9. The sample cell filling device of claim 8, wherein the longitudinal axis of the at least one filling port when the sample cell is positioned in the sample filling device is substantially at 90 degrees to the horizontal plane of the sample cell filling device.

10. The sample cell filling device of claim 1, wherein the inclined angle is between about 10 to 50 degrees relative to a horizontal plane.

11. A sample cell filling device for filling a sample cell externally of and to be used remotely in a polarimeter comprising:

a liquid-sealed housing having a recess for receiving the sample cell at an angle between about 10 to about 50 degrees relative to a horizontal plane, the sample cell having a first optical window at a first end and a second optical window at a second end along a longitudinal axis thereof;

a light source positioned within the liquid-sealed housing and operable to transmit light from the first optical window to the second optical window;

a focusing lens positioned within the sealed housing and to receive light from the second optical window;

a viewing screen, wherein the viewing screen receives light from the focusing lens, and further wherein the viewing screen is physically adapted to diffuse the light it receives.

12. The sample cell filling device of claim 11, wherein the viewing screen comprises ground glass, wherein the ground glass diffuses the light received at the viewing screen.

13. The sample cell filling device of claim 11, further comprising an aperture positioned at a focal point of the focusing lens.

14. The sample cell filling device of claim 13, further comprising a mirror disposed in an optical path between the aperture and the diffuser viewing screen to reflect the light from the aperture to the diffuser viewing screen.

15. The sample cell filling device of claim 11, further comprising the sample cell having a first filling port located near the first end and a second filling port located near the second end, wherein at least one of the first and second filling ports is inclined relative to the longitudinal axis of the sample cell such that the sample makes only a single change of direction when the sample is being filled in the sample cell.

\* \* \* \* \*